US006596526B1

(12) United States Patent
Plaimauer et al.

(10) Patent No.: US 6,596,526 B1
(45) Date of Patent: Jul. 22, 2003

(54) FURIN POLYPEPTIDES WITH IMPROVED CHARACTERISTICS

(75) Inventors: Barbara Plaimauer, Vienna (AT); Uwe Schlokat, Orth/Donau (AT)

(73) Assignee: Baxter Aktiengesellschaft, Vienna (AT)

( * ) Notice: Subject to any disclaimer, the term of this patent is extended or adjusted under 35 U.S.C. 154(b) by 0 days.

(21) Appl. No.: 09/592,480

(22) Filed: Jun. 9, 2000

(51) Int. Cl.[7] ......................... C12N 9/64; C12N 15/57; C12N 15/62; C12N 15/79; C12N 15/84

(52) U.S. Cl. .................. 435/226; 435/69.1; 435/69.7; 435/252.3; 435/320.1; 435/471; 536/23.2; 536/23.4

(58) Field of Search .................. 435/69.1, 69.7, 435/226, 471, 252.3, 320.1; 536/23.2

(56) References Cited

U.S. PATENT DOCUMENTS

| | | | | |
|---|---|---|---|---|
| 5,460,950 A | * | 10/1995 | Barr et al. | 435/69.1 |
| 5,965,425 A | * | 10/1999 | Barr et al. | 435/226 |
| 5,986,079 A | * | 11/1999 | Barr et al. | 536/23.2 |
| 6,210,929 B1 | * | 2/2001 | Schlokat et al. | 435/69.7 |

FOREIGN PATENT DOCUMENTS

| | | |
|---|---|---|
| JP | WO 97/41250 | 11/1997 |
| WO | WO90/11092 | 10/1990 |
| WO | WO 91/06314 | 5/1991 |
| WO | WO 92/09698 | 6/1992 |
| WO | WO 93/09236 | 5/1993 |

OTHER PUBLICATIONS

Alting–Mees, M. A., et al.; pBluescript II: gene mapping vectors; *Nucleic Acids Research*; vol. 17, No. 22, pp. 9494 (1989).

Anderson, E., et al.; Activation of the furin endoprotease is a multiple–step process: requirements for acidification and internal propeptide cleavage; *EMBO J.*; pp. 1508–1518 (1997).

Ausubel, et al.; Mutagenesis of Cloned DNA; *Current Protocols in Molecular Biology*, vol. 1 ch. 8 (1989).

Fuller, R., et al.; Intracellular Targeting and Structural Conservation of a Prohormone–Processing Endoprotease; *Science*; vol. 246, pp. 482–486 (1989).

Kyte, J., et al.; A Simple Method for Displaying the Hydropathic Character of a Protein; *J. Mol. Biol.*; vol. 157, pp. 105–132 (1982).

Leduc, R., et al.; Activation of Human Furin Precursor Processing Endoprotease Occurs by an Intramolecular Autoproteolytic Cleavage; *J. Biol. Chem.*; vol. 267, pp. 14304–14308 (1992).

Moehring, J., et al.; Strains of CHO–K1 Cells Resistant to Pseudomonas Exotoxin A and Cross–Resistant to Diphtheria Toxin and Viruses; *Infection and Immunity*; vol. 41, pp. 998–1009 (1983).

Molloy, S. S., et al.; Intracellular trafficking and activation of the furin proprotein convertase; localization to the TGN and recycling from the cell surface; *EMBO J.*; vol. 13, pp. 18–33 (1994).

(List continued on next page.)

*Primary Examiner*—Nashaat T. Nashed
*Assistant Examiner*—William W. Moore
(74) *Attorney, Agent, or Firm*—Michael F. Fedrick; Townsend and Townsend and Crew

(57) ABSTRACT

The present invention comprises a furin polypeptide having a modified amino acid sequence between the middle, homo-B-domain and the transmembrane domain compared to wild-type furin which retains proteolytic activity but is secreted at lower levels in cell culture compared to wild-type furin. Additionally, the invention includes nucleic acid molecules encoding such furin polypeptides, vectors and host cells comprising said nucleic acid molecules, compositions comprising said furin polypeptide and methods for producing such compositions.

15 Claims, 6 Drawing Sheets

OTHER PUBLICATIONS

Nakayama, K.; Furin: a mammalian subtillsin/Kex2p–like endoprotease involved in processing of a wide variety of precursor proteins; *Biochem J.*; vol. 327, pp. 625–635 (1997).

Preininger, A. et al.; Strategies for recombinant Furin employment in a biotechnological process: complete target protein precursor cleavage; *Cytotechnol.*; vol. 30, pp. 1–15 (1999).

Rehemtulla, A., et al.; Preferred Sequence Requirments for Cleavage of Pro–von Willebrand Factor by Propeptide–Processing Enzymes; *Blood*; vol. 79, pp. 2349–2355 (1992).

Rost, B., et al.; Improved prediction of protein secondary structure by use of sequence profiles and neural networks; *Proc. Natl. Acad. Sci. USA*; vol. 90 pp. 7558–7562 (1993).

Rost, B., et al.; Combining Evolutionary Information and Neural Networks to Predict Protein Secondary Structure; *Proteins: Structure, Function and Genetics*; vol. 19, pp. 55–72 (1994).

Schafer, W., et al.; Two independent targeting signals in the cytoplasmic domain determine trans–Golgi network localization and endosomal trafficking of the proprotein convertase furin; *EMBO J.*; vol. 11, pp. 2424–2435 (1995).

Schlokat, U., et al.; Production of highly homogeneous and structurally intact recombinant von Willebrand Factor multimers by furin–mediated propeptide removal in vitro; *Biotechnol. Appl. Biochem.*; vol. 24, pp. 257–267 (1996).

Seidah, N., et al.; Eukaryotic protein processing: endoproteolysis of precursor proteins; *Current Opinions in Biotechnology*; vol. 8, pp. 602–607 (1997).

Seidah, N., et al.; The family of subtilsin/kexin like proprotein and pro–hormone convertases: Divergent or shared functions; *Biochem*; vol. 76, pp. 197–209 (1994).

Short, J., et al.; X Zap: a bacteriophage X expression vector with in vivo excision properties; *Nucleic Acids Research*; vol. 16, No. 15, pp. 7583–7600 (1988).

Teuchert, M., et al.; Sorting of Furin at the Trans–Golgi Network; *J. Biol. Chem.*; vol. 274, pp. 8199–8207 (1999).

Urlaub, G., et al.; Isolation of Chinese hamster cell mutants deficient in dihydrofolate reductase activity; *Proc. Natl. Acad. Sci. USA*; vol. 77 No. 7, pp. 4216–4220 (1980).

Van den Ouweland, A., et al.; Structural hornology between the human fur gene product and the subtilsin–like protease encoded by yeast KEX2; *Nucleic Acid Res.*; vol. 18, No. 3, pp. 664 (1990).

Vey, M., et al.; Maturation of the trans–Golgi Network Protease Furin: Compartmentalization of Propeptide Removal, Substrate Cleavage, and COOH–terminal Truncation; *J. Cell. Biol.*; vol. 127 No. 6, pp. 1829–1842 (1994).

Vidricaire, G., et al.; Characterization of a secreted from of human furin endoprotease; *Biochem. Biphys. Res. Comm.*; vol. 195 No. 2, pp. 1011–1018 (1993).

Voorhees, P., et al.; An acidic sequence within the cytoplasmic domain of furin functions as a determinant of transGolgi network localization and internalization from the cell surface; *EMBO J.*; vol. 20, pp. 4961–4975 (1995).

Wise, R., et al.; Expression of a human proprotein processing enzyme:Correct cleavage of the von Willebrand factor precursor at a paired basic amino acid site; *Proc. Natl. Acad. Sci.USA*; vol. 87, pp. 9378–9382 (1990).

Lehninger, A.; *Biochemie*; VCH, pp. 102–107 (1985).

Karlson P., et al.; *Kurzes Lehrbuch der Biochemie*; Georg Thieme Verlag, pp. 29–32 (1994).

Spence, MJ et al, "Furin Endoprotease", abstract, *database EMBL*, Nov. 1, 1996.

Hoechst, "Human BMP processing enzyme furin", database EMBL, May 8, 1998 abstract (also see WO97/41250 above).

Smeekens, S.P. et al, "Identification of a cDNA Encoding a Second Putative Prohormone Convertase Related to PC2 in AtT20 Cells and Islets of Langerhans":, Proc. Natl. Acad. Sci, USA, vol. 88, pp. 340–344, Jan. 1991.

Plaimauer et al, "Shed'Furin: Mapping of the Cleavage determinants and identification of its C–terminus," Biochem J, vol. 354, pp. 689–695, 2001.

\* cited by examiner

Human furin wild-type 794 aa; Listed from: 1 to: 794

```
MELRPWLLWV VAATGTLVLL AADAQGQKVF TNTWAVRIPG GPAVANSVAR KHGFLNLGQI FGDYYHFWHR
        10         20         30         40         50         60         70

GVTKRSLSPH RPRHSRLQRE PQVQWLEQQV AKRRTKRDVY QEPTDPKFPQ QWYLSGVTQR DLNVKAAWAQ
        80         90        100        110        120        130        140

GYTGHGIVVS ILDDGIEKNH PDLAGNYDPG ASFDVNDQDP DPQPRYTQMN DNRHGTRCAG EVAAVANNGV
       150        160        170        180        190        200        210

CGVGVAYNAR IGGVRMLDGE VTDAVEARSL GLNPNHIHIY SASWGPEDDG KTVDGPARLA EEAFFRGVSQ
       220        230        240        250        260        270        280

GRGGLGSIFV WASGNGGREH DSCNCDGYTN SIYTLSISSA TQFGNVPWYS EACSSTLATT YSSGNQNEKQ
       290        300        310        320        330        340        350

IVTTDLRQKC TESHTGTSAS APLAAGIIAL TLEANKNLTW RDMQHLVVQT SKPAHLNAND WATNGVGRKV
       360        370        380        390        400        410        420

SHSYGYGLLD AGAMVALAQN WTTVAPQRKC IIDILTEPKD IGKRLEVRKT VTACLGEPNH ITRLEHAQAR
       430        440        450        460        470        480        490

LTLSYNRRGD LAIHLVSPMG TRSTLLAARP HDYSADGFND WAFMTTHSWD EDPSGEWVLE IENTSEANNY
       500        510        520        530        540        550        560

GTLTKFTLVL YGTAPEGLPV PPESSGCKTL TSSQACVVCE EGFSLHQKSC VQHCPPGFAP QVLDTHYSTE
       570        580        590        600        610        620        630

NDVETIRASV CAPCHASCAT CQGPALTDCL SCPSHASLDP VEQTCSRQSQ SSRESPPQQQ PPRLPPEVEA
       640        650        660        670        680        690        700

GQRLRAGLLP SHLPEVVAGL SCAFIVLVFV TVFLVLQLRS GFSFRGVKVY TMDRGLISYK GLPPEAWQEE
       710        720        730        740        750        760        770

CPSDSEEDEG RGERTAFIKD QSAL
       780        790
```

Figure 1

SEQUENCE LISTING

<160> NUMBER OF SEQ ID NOS: 21

<210> SEQ ID NO 1
<211> LENGTH: 794
<212> TYPE: PRT
<213> ORGANISM: Human

<400> SEQUENCE: 1

```
Met Glu Leu Arg Pro Trp Leu Leu Trp Val Val Ala Ala Thr Gly Thr
1               5                   10                  15

Leu Val Leu Leu Ala Ala Asp Ala Gln Gly Gln Lys Val Phe Thr Asn
            20                  25                  30

Thr Trp Ala Val Arg Ile Pro Gly Gly Pro Ala Val Ala Asn Ser Val
        35                  40                  45

Ala Arg Lys His Gly Phe Leu Asn Leu Gly Gln Ile Phe Gly Asp Tyr
    50                  55                  60

Tyr His Phe Trp His Arg Gly Val Thr Lys Arg Ser Leu Ser Pro His
65                  70                  75                  80

Arg Pro Arg His Ser Arg Leu Gln Arg Glu Pro Gln Val Gln Trp Leu
                85                  90                  95

Glu Gln Gln Val Ala Lys Arg Arg Thr Lys Arg Asp Val Tyr Gln Glu
            100                 105                 110

Pro Thr Asp Pro Lys Phe Pro Gln Gln Trp Tyr Leu Ser Gly Val Thr
        115                 120                 125

Gln Arg Asp Leu Asn Val Lys Ala Ala Trp Ala Gln Gly Tyr Thr Gly
    130                 135                 140

His Gly Ile Val Val Ser Ile Leu Asp Asp Gly Ile Glu Lys Asn His
145                 150                 155                 160

Pro Asp Leu Ala Gly Asn Tyr Asp Pro Gly Ala Ser Phe Asp Val Asn
                165                 170                 175

Asp Gln Asp Pro Asp Pro Gln Pro Arg Tyr Thr Gln Met Asn Asp Asn
            180                 185                 190

Arg His Gly Thr Arg Cys Ala Gly Glu Val Ala Ala Val Ala Asn Asn
        195                 200                 205

Gly Val Cys Gly Val Gly Val Ala Tyr Asn Ala Arg Ile Gly Gly Val
    210                 215                 220

Arg Met Leu Asp Gly Glu Val Thr Asp Ala Val Glu Ala Arg Ser Leu
225                 230                 235                 240

Gly Leu Asn Pro Asn His Ile His Ile Tyr Ser Ala Ser Trp Gly Pro
                245                 250                 255
```

-continued

Glu Asp Asp Gly Lys Thr Val Asp Gly Pro Ala Arg Leu Ala Glu Glu
            260                 265                 270

Ala Phe Phe Arg Gly Val Ser Gln Gly Arg Gly Gly Leu Gly Ser Ile
            275                 280                 285

Phe Val Trp Ala Ser Gly Asn Gly Gly Arg Glu His Asp Ser Cys Asn
            290                 295                 300

Cys Asp Gly Tyr Thr Asn Ser Ile Tyr Thr Leu Ser Ile Ser Ser Ala
305                 310                 315                 320

Thr Gln Phe Gly Asn Val Pro Trp Tyr Ser Glu Ala Cys Ser Ser Thr
            325                 330                 335

Leu Ala Thr Thr Tyr Ser Ser Gly Asn Gln Asn Glu Lys Gln Ile Val
            340                 345                 350

Thr Thr Asp Leu Arg Gln Lys Cys Thr Glu Ser His Thr Gly Thr Ser
            355                 360                 365

Ala Ser Ala Pro Leu Ala Ala Gly Ile Ile Ala Leu Thr Leu Glu Ala
            370                 375                 380

Asn Lys Asn Leu Thr Trp Arg Asp Met Gln His Leu Val Val Gln Thr
385                 390                 395                 400

Ser Lys Pro Ala His Leu Asn Ala Asn Asp Trp Ala Thr Asn Gly Val
            405                 410                 415

Gly Arg Lys Val Ser His Ser Tyr Gly Tyr Gly Leu Leu Asp Ala Gly
            420                 425                 430

Ala Met Val Ala Leu Ala Gln Asn Trp Thr Thr Val Ala Pro Gln Arg
            435                 440                 445

Lys Cys Ile Ile Asp Ile Leu Thr Glu Pro Lys Asp Ile Gly Lys Arg
450                 455                 460

Leu Glu Val Arg Lys Thr Val Thr Ala Cys Leu Gly Glu Pro Asn His
465                 470                 475                 480

Ile Thr Arg Leu Glu His Ala Gln Ala Arg Leu Thr Leu Ser Tyr Asn
            485                 490                 495

Arg Arg Gly Asp Leu Ala Ile His Leu Val Ser Pro Met Gly Thr Arg
            500                 505                 510

Ser Thr Leu Leu Ala Ala Arg Pro His Asp Tyr Ser Ala Asp Gly Phe
            515                 520                 525

Asn Asp Trp Ala Phe Met Thr Thr His Ser Trp Asp Glu Asp Pro Ser
            530                 535                 540

Gly Glu Trp Val Leu Glu Ile Glu Asn Thr Ser Glu Ala Asn Asn Tyr
545                 550                 555                 560

Gly Thr Leu Thr Lys Phe Thr Leu Val Leu Tyr Gly Thr Ala Pro Glu
            565                 570                 575

Gly Leu Pro Val Pro Pro Glu Ser Ser Gly Cys Lys Thr Leu Thr Ser
            580                 585                 590

Ser Gln Ala Cys Val Val Cys Glu Glu Gly Phe Ser Leu His Gln Lys
            595                 600                 605

Ser Cys Val Gln His Cys Pro Pro Gly Phe Ala Pro Gln Val Leu Asp
            610                 615                 620

Thr His Tyr Ser Thr Glu Asn Asp Val Glu Thr Ile Arg Ala Ser Val
625                 630                 635                 640

Cys Ala Pro Cys His Ala Ser Cys Ala Thr Cys Gln Gly Pro Ala Leu
            645                 650                 655

Thr Asp Cys Leu Ser Cys Pro Ser His Ala Ser Leu Asp Pro Val Glu
            660                 665                 670

Gln Thr Cys Ser Arg Gln Ser Gln Ser Ser Arg Glu Ser Pro Pro Gln

-continued

```
            675                 680                 685
Gln Gln Pro Pro Arg Leu Pro Pro Glu Val Glu Ala Gly Gln Arg Leu
            690                 695                 700

Arg Ala Gly Leu Leu Pro Ser His Leu Pro Val Val Ala Gly Leu
705                 710                 715                 720

Ser Cys Ala Phe Ile Val Leu Val Phe Val Thr Val Phe Leu Val Leu
                725                 730                 735

Gln Leu Arg Ser Gly Phe Ser Phe Arg Gly Val Lys Val Tyr Thr Met
            740                 745                 750

Asp Arg Gly Leu Ile Ser Tyr Lys Gly Leu Pro Pro Glu Ala Trp Gln
            755                 760                 765

Glu Glu Cys Pro Ser Asp Ser Glu Asp Gly Arg Gly Glu Arg
            770                 775                 780

Thr Ala Phe Ile Lys Asp Gln Ser Ala Leu
785                 790

<210> SEQ ID NO 2
<211> LENGTH: 5
<212> TYPE: PRT
<213> ORGANISM: Artificial Sequence
<220> FEATURE:
<223> OTHER INFORMATION: substitution region

<400> SEQUENCE: 2

Glu Ala Met His Ala
1               5

<210> SEQ ID NO 3
<211> LENGTH: 5
<212> TYPE: PRT
<213> ORGANISM: Artificial Sequence
<220> FEATURE:
<223> OTHER INFORMATION: substitution region

<400> SEQUENCE: 3

Ala Trp Phe Gln Trp
1               5

<210> SEQ ID NO 4
<211> LENGTH: 20
<212> TYPE: PRT
<213> ORGANISM: Artificial Sequence
<220> FEATURE:
<223> OTHER INFORMATION: substitution region

<400> SEQUENCE: 4

Ala Gln Met Trp His Glu Ala Met Glu Phe Trp Ala Met Gln Phe Glu
1               5                   10                  15

Ala Met His Ala
            20

<210> SEQ ID NO 5
<211> LENGTH: 10
<212> TYPE: PRT
<213> ORGANISM: Artificial Sequence
<220> FEATURE:
<223> OTHER INFORMATION: substitution region

<400> SEQUENCE: 5

Ala Glu Met Trp His Gln Ala Met Glu Val
1               5                   10
```

```
<210> SEQ ID NO 6
<211> LENGTH: 5
<212> TYPE: PRT
<213> ORGANISM: Artificial Sequence
<220> FEATURE:
<223> OTHER INFORMATION: substitution region

<400> SEQUENCE: 6

Ser Tyr Asn Pro Gly
1               5

<210> SEQ ID NO 7
<211> LENGTH: 5
<212> TYPE: PRT
<213> ORGANISM: Artificial Sequence
<220> FEATURE:
<223> OTHER INFORMATION: substitution region

<400> SEQUENCE: 7

Ser Tyr Gln Pro Asp
1               5

<210> SEQ ID NO 8
<211> LENGTH: 10
<212> TYPE: PRT
<213> ORGANISM: Artificial Sequence
<220> FEATURE:
<223> OTHER INFORMATION: substitution region

<400> SEQUENCE: 8

Gly Ser Pro Tyr Gln Thr Asn Gly Pro Ser
1               5                   10

<210> SEQ ID NO 9
<211> LENGTH: 10
<212> TYPE: PRT
<213> ORGANISM: Artificial Sequence
<220> FEATURE:
<223> OTHER INFORMATION: substitution region

<400> SEQUENCE: 9

Gly Ser Pro Asn Ser Gln Pro Tyr Asp Gly
1               5                   10

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10 ggggatccc tctggcgagt gg                                         22

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
cggggactct gcgctgctct g                                         21

<210> SEQ ID NO 12
<211> LENGTH: 21
<212> TYPE: DNA
```

```
<213> ORGANISM: Artificial Sequence
<220> FEATURE:
<223> OTHER INFORMATION: primer

<400> SEQUENCE: 12
cagagcagcg cagagtcccc g                                         21

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
gggggatccc cgcggcctag g                                         21

<210> SEQ ID NO 14
<211> LENGTH: 45
<212> TYPE: DNA
<213> ORGANISM: Artificial Sequence
<220> FEATURE:
<223> OTHER INFORMATION: primer

<400> SEQUENCE: 14
caggccatgg aggtgcacct gcctgaggtg gtggccggcc tcagc               45

<210> SEQ ID NO 15
<211> LENGTH: 45
<212> TYPE: DNA
<213> ORGANISM: Artificial Sequence
<220> FEATURE:
<223> OTHER INFORMATION: primer

<400> SEQUENCE: 15
gtgccacatc tcggcccct cagggcggt gccatagagt acgag                 45

<210> SEQ ID NO 16
<211> LENGTH: 45
<212> TYPE: DNA
<213> ORGANISM: Artificial Sequence
<220> FEATURE:
<223> OTHER INFORMATION: primer

<400> SEQUENCE: 16
cagccctacg acggccacct gcctgaggtg gtggccggcc tcagc               45

<210> SEQ ID NO 17
<211> LENGTH: 45
<212> TYPE: DNA
<213> ORGANISM: Artificial Sequence
<220> FEATURE:
<223> OTHER INFORMATION: primer

<400> SEQUENCE: 17
gctgttgggg ctgccccct cagggcggt gccatagagt acgag                 45

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
cacctgcctg aggtggtggc c                                         21
```

```
<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
cccctcaggg gcggtgccat                                               20

<210> SEQ ID NO 20
<211> LENGTH: 10
<212> TYPE: PRT
<213> ORGANISM: Artificial Sequence
<220> FEATURE:
<223> OTHER INFORMATION: insertion

<400> SEQUENCE: 20

Ala Glu Met Trp His Gln Ala Met Glu Val
1               5                   10

<210> SEQ ID NO 21
<211> LENGTH: 10
<212> TYPE: PRT
<213> ORGANISM: Artificial Sequence
<220> FEATURE:
<223> OTHER INFORMATION: insertion

<400> SEQUENCE: 21

Gly Ser Pro Asn Ser Gln Pro Tyr Asp Gly
1               5                   10
```

FURIN POLYPEPTIDES WITH IMPROVED CHARACTERISTICS

BACKGROUND OF THE INVENTION

The present invention relates to new furin polypeptides. Furin, also called PACE (for paired basic amino acid cleavage enzyme), belongs to the family of mammalian subtilisin-like proprotein convertases (SPC or PC) These proteins have been implicated in the endoproteolytic maturation processing of inactive precursor proteins at single, paired or multiple basic consensus sites within the secretory pathway (reviewed in Nakayama, 1997, Biochem.J., 327, pp. 625–635; (Seidah and Chretien, Current Opinions in Biotechnology,8, 1997, pp. 602–607). Seven distinct members of this family have been identified to date, including furin, PC1 (also known as PC3), PC2, PACE4, PC4, PC5 (also known as PC6), PC7 (or LPC, PC8, or SPC7), each of which exhibits unique tissue distribution, although overlapping functional redundancy of various PCs in some tissues may occur (Seidah et al., Biochem.,1994, 76, pp. 197–209).

Furin is ubiquitously expressed in all mammalian tissues and cell lines which have been examined, and is capable of processing a wide range of bioactive precursor proteins in the secretory pathway, including growth factors, hormones, plasma proteins, receptors, viral envelope glycoproteins and bacterial toxins. It is a calcium-dependent serine endoprotease structurally arranged into several domains, namely a signal peptide, propeptide, catalytic domain, middle domain, (also termed homo-B or P-domain), the C-terminally located cysteine-rich domain, transmembrane domain and the cytoplasmic tail. Upon transit of the newly synthesized furin precursor from the endoplasmic reticulum to the Golgi compartment, the propeptide is autocatalytically removed in a two step processing event (Leduc et al., J.Biol.Chem., 267, 1992, pp. 14304–14308; Anderson et al., EMBO J., 1997, pp. 1508–1518).

Furin is predominantly localized to the trans-Golgi network (TGN), but it also cycles between the TGN and the cell surface via endosomal vesicles, thereby processing both precursor proteins during their transport through the constitutive secretory pathway as well as molecules entering the endocytic pathway. The cellular distribution of furin to the varied processing compartments is apparently directed by defined structural features within its cytoplasmic tail (Schäfer et al., EMBO J.,11, 1995, pp. 2424–2435; Voorhees et al., EMBO J., 20, 1995, pp. 4961–4975; Teuchert et al., J.Biol.Chem., 274, 1999, pp. 8199–8207). Deletion of the cytoplasmic domain results in a truncated furin polypeptide located primarily in the plasma membrane, to which it is transported probably by a default pathway, incapable of recycling to the TGN due to the loss of regulative sequence motifs within the cytoplasmic domain (Molloy et al., EMBO J., 13, 1994, pp. 18–33; Schäfer et al., EMBO J., 14, 1995, pp. 2424–2435).

The C-terminal domains have been found to be dispensable for the functional activity of furin. Mutant furin lacking the transmembrane domain and the cytoplasmic tail, was found to be readily released into cell culture medium while still exhibiting significant activity. High levels of expression of full length recombinant furin have resulted in the natural secretion of a truncated furin form, called 'shed' furin, which lacks the transmembrane domain and the cytoplasmic tail (Wise et al., Proc.Natl.Acad.Sci., 87, 1990, pp. 9378–9382; Rehemtulla and Kaufman, Blood, 79, 1992, pp. 2349–2355; Vidricaire et al., Biochem.Biophys.Res.Comm., 195, 1993 pp. 1011–1018; Vey et al., J.Cell.Biol., 127, 1994, pp. 1829–1842; Preininger et al.,Cytotechnol., 30, 1999, pp. 1–15). It remains an open question as to whether furin shedding is due to saturating cellular retrieval mechanisms, whether it represents a protection mechanism of the host cell against excess protease, or whether is part of a natural regulatory process modulating intracellular furin concentration/activity by secretion. The isolation of a truncated endogenous furin from the Golgi fraction of bovine kidney cells may support the view that shedding is not solely an artificial secretion process caused by overexpression (Vey et al., 1994). Conversion of furin into the soluble secreted form was shown to occur intracellularly within an acidic compartment which requires the presence of calcium (Vey et al., 1994).

The presence of a C-terminal truncated and hence soluble form of furin that remains active, however, has been detected almost exclusively in conditioned medium of cells recombinantly overexpressing native full-length furin (Wise et al., 1990; Rehemtulla and Kaufman, 1992; Vidricaire et al., 1993; Vey et al., 1994; Preininger et al., 1999).

Other prior art describing furin polypeptides includes WO 91/06314, which describes a fragment of furin consisting of amino acids 108–464, thus lacking part of the homo-B domain, the cysteine-rich region, the transmembrane domain and the cytoplasmic tail. WO 92/09698 discloses full length furin and furin lacking the transmembrane domain. In addition, Preininger et al. (Cytotechnology 30, 1999, pp. 1–15) describe furin mutants lacking the cysteine rich region, the trans-membrane domain and the cytosolic domain. Cells expressing such mutants contained increased intracellular concentrations of the furin derivatives but varying levels of secretion. The authors stated that the lack of extracellular accumulation of these molecules suggested that these molecules were most likely degraded. The authors stated further that full length recombinant furin, located intracellularly, seems to be largely inactive and that there is a potential toxicity of larger amounts of full length furin to its host cell.

SUMMARY OF THE INVENTION

We have found that soluble furin in a cell culture medium can cause proteins which are not naturally processed by furin to be unspecifically cleaved. For example, although native Factor VIII is not naturally processed by furin, Factor VIII can become a target for inadvertant processing by soluble furin when exposed to furin for an extended period of time, e.g. in a cell culture medium. This leads to, a reduced yield of structurally intact Factor VIII protein in such cell culture medium. This can be the case when Factor VIII is coexpressed together with a natural substrate of furin, e.g. von Willebrand Factor, or when recombinant proteins which are naturally processed by furin are exposed to furin for an extended period of time so that in addition inadvertent sites are cleaved.

The present invention reduces or prevents unspecific cleavage of proteins in cell culture through the use of modified furin polypeptides which have proteolytic activity but which are not secreted into culture medium by host cells or are secreted in reduced amounts compared to the secretion of wild-type furin. Such furin polypeptides have been found not to be toxic to host cells even when expressed intracellularly in high amounts.

Accordingly, the present invention provides a furin polypeptide having a modified amino acid sequence compared to that of wild-type furin between homo-B-domain and the transmembrane domain, that is, between amino acids Ala 557 and Leu 713 according to the amino acid sequence presented in FIGS. 1 and 2. It has been surprisingly found that furin polypeptides having such a modified amino acid sequence have proteolytic activity similar to that of native (i.e., wild-type) furin, but are secreted by host cells expressing such furin polypeptides into cultivation medium in substantially reduced amounts compared to native furin.

It is another aspect of the invention that the furin polypeptides according to the invention can be expressed in high amounts in a cell without being substantially toxic to the cell. In still a further aspect, the physiological cleavage properties of the modified furin protein are still present, but inadvertent cleavage of secreted or extracellularly localized proteins in a cell culture medium is highly reduced since less or no furin is present in the medium.

Additionally, a further advantage of the furin polypeptide of the present invention is that although the proteolytic processing of furin-dependent proteins can occur intracellularly, unspecific processing of proteins by furin can be at least reduced if not completely eliminated. Therefore, unspecific cleavage of proteins which might occur when proteins are exposed to soluble furin in a conditioned medium in cell culture is avoided by the furin polypeptide according to the present invention.

In another aspect, the invention provides a recombinant polynucleotide encoding the furin polypeptide according to the present invention. In yet another aspect, the invention provides a method for producing the furin polypeptide according to the present invention, a recombinant vector comprising the polynucleotide sequence encoding the furin polypeptide according to the invention, a host cell comprising such vector, and a preparation comprising the furin polypeptide of the present invention.

DESCRIPTION OF THE DRAWINGS

FIG. 1 shows the amino acid sequence of human wild-type furin (SEQ ID NO:1).

FIG. 5A is a photograph of an SDS-PAGE gel showing shed recombinant furin (rfurin) in conditioned medium of transiently transfected HEK 293 cells;

FIG. 5B is a photograph of an SDS-PAGE gel showing intracellular rfurin expression in HEK 293 lysates; and FIG. 5C shows the results of an in vitro furin assay using conditioned medium and fluorogenic substrate (in arbitrary units).

DETAILED DESCRIPTION OF THE INVENTION

Furin Polypeptides

Figure 2:
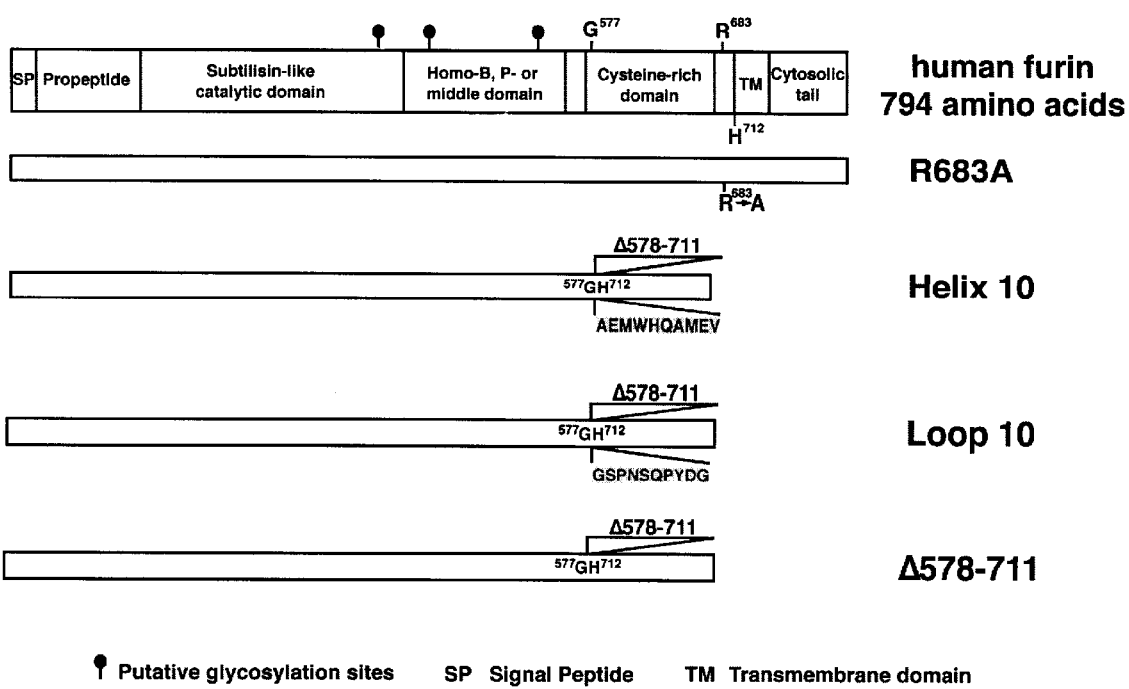
FIG. 2 is a schematic representation of the amino acid sequences of wild-type furin and furin mutants.
Figure 3:
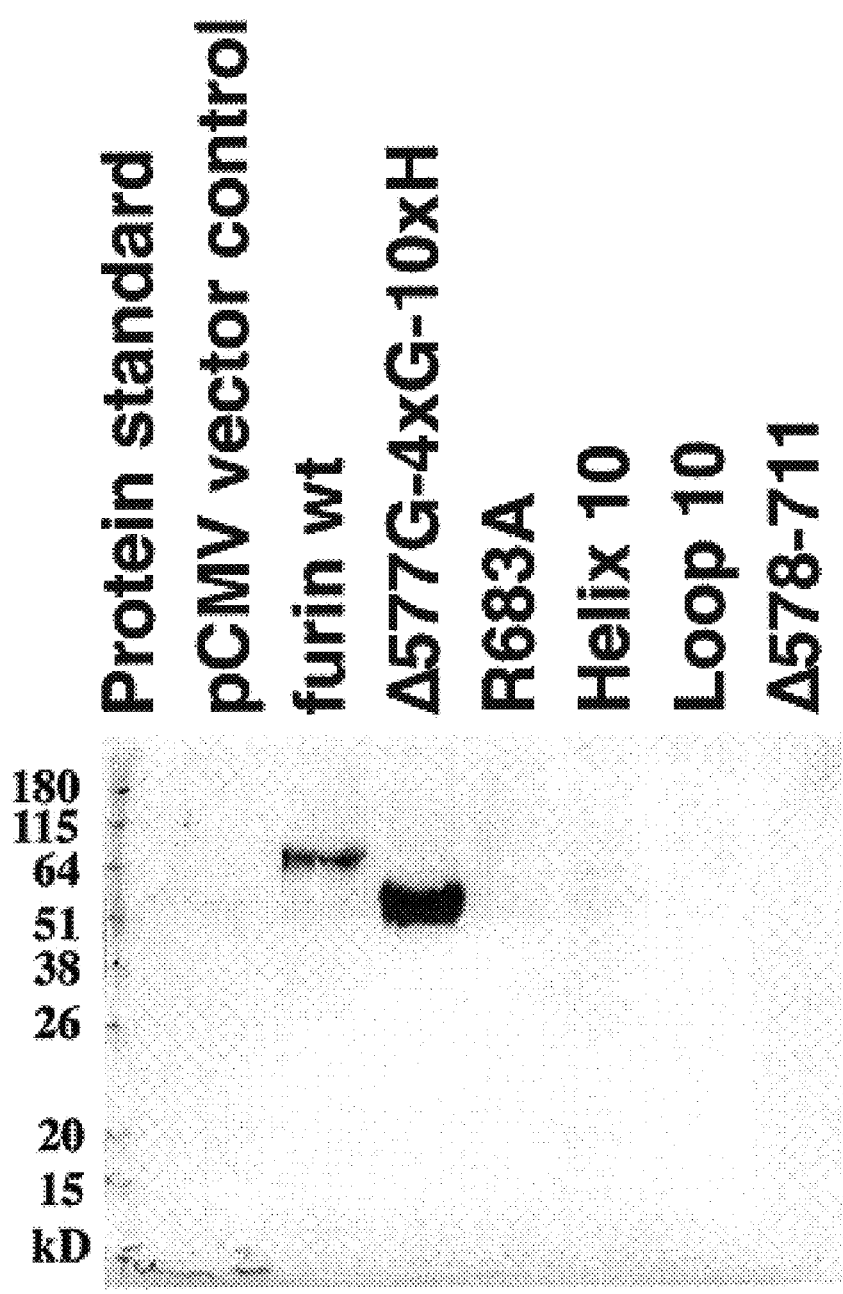
FIG. 3 is a photograph of an SDS-PAGE gel showing shed furin in a conditioned medium in which FD11-CHO-rvWF cells transiently transfected with furin constructs were grown.
Figure 4:
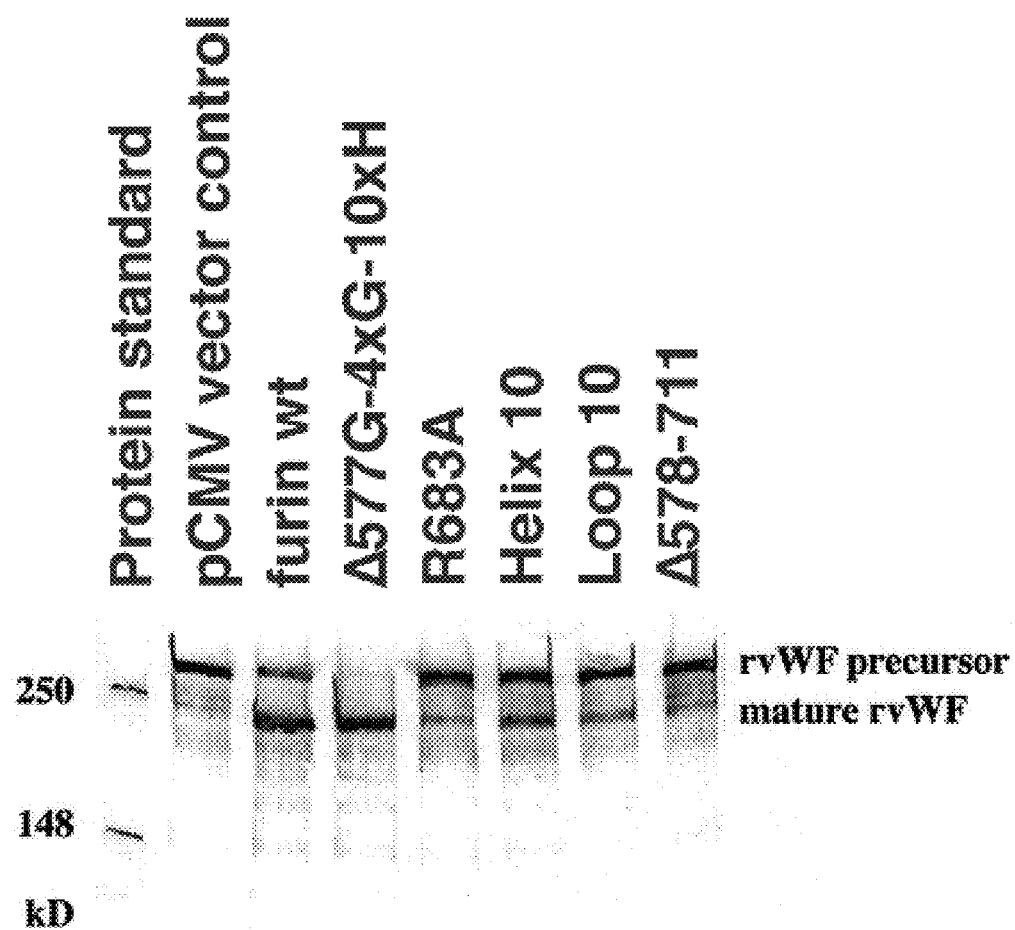
FIG. 4 is a photograph of an SDS-PAGE gel showing the processing of rvWF precursor in FD11-CHO-rvWF cells transiently transfected with furin constructs.

The present invention comprises furin polypeptides which have a modified amino acid sequence between amino acids Ala 557 and Leu 713 compared to the amino acid sequence of wild-type mammalian furin, such as human furin (the amino acid sequence of which is shown in FIG. 1). For purposes of the present disclosure, a furin polypeptide shall refer to a polypeptide comprising at least a portion of the amino acid sequence of a wild-type mammalian furin protein which has proteolytic activity. In a preferred embodiment the modification in a furin polypeptide according to the present invention is located between amino acids Ala 557 and Leu 713. In an alternative embodiment, the modification is at Arg 683. In still another embodiment, the amino acids between Gly 577 and His712 are deleted.

In the instant disclosure, the terms "modified" and "modification" shall mean, with respect to the amino acid sequence of a furin polypeptide, an addition, deletion or substitution of one or more amino acids. Such a modification can be carried out by, for instance, directed mutagenesis or PCR or other methods of genetic engineering known in the art which are suitable for specifically changing a DNA sequence in order to direct a change in the amino acid sequence of the resulting polypeptide (Current Protocols in Molecular Biology, vol. 1, ch. 8 (Ausubel et al. eds., J. Wiley and Sons, 1989 & Supp. 1990–93); Protein Engineering (Oxender & Fox eds., A. Liss, Inc., 1987). The modifications of the present invention are in the region between the homo-B-domain and the transmembrane domain, i.e. the region between the amino acids Ala 557 and Leu 713, of the furin molecule.

Preferably, the furin polypeptide of the present invention has amino acid substitutions and/or additions creating loop or alpha-helix structures. It is well known from the prior art that amino acids can form several different secondary structures in polypeptides, i.e. helical or looped structures (Lehninger A., "Biochemie", VCH, 1985, pp. 102–107; Karlson P. et al., "Kurzes Lehrbuch der Biochemie, Georg Thieme Verlag, 1994; pp. 29–32). These structures can be produced by selecting specific amino acids which form, for example, alpha helices and loops and thereby developing structures like helices or loops in the resulting polypeptide (Rost B. and Sander C., Proc.Natl.Acad.Sci., 1993, pp. 7558–7562, Rost B. and Sander C., 1994, Proteins: Structure, Function and Genetics, 19, pp. 55–72). Additionally, according to Kyte J. and Doolittle R. (1983, J.Mol.Biol., 157, pp. 105–132) such amino acids may be selected based on their hydropathy values, in view of the knowledge that amino acids showing negative hydropathy values are hydrophilic, allowing these side chains access to the aqueous solvent, whereas amino acids showing positive hydropathy values are hydrophobic amino acids which tend to comprise interior portions of the proteins. Additionally, it is known that amino acids showing very high positive or negative hydropathy values are preferred targets for various proteases.

Therefore, in a preferred embodiment, there is an insertion of several amino acids, preferably between 5 and 30, more preferably between 10 to 20, which produce a loop or helix structure in the modified furin polypeptide of the present invention.

In an alternative embodiment, the insertion of amino acids results in a helix structure. In such an embodiment the amino acids are preferably selected from the group consisting of alanine (A), leucine (L), phenylalanine (F), tryptophan (W), methionine (M), histidine (H), glutamine (Q), valine (V) and glutamic acid (E). For example, the amino acids 558 to 738, preferably amino acids 578 to 711 are substituted by the amino acid sequences EAMHA (SEQ ID NO:2), AWFQW (SEQ ID NO:3) OR AQMWHEAMEFWAMQFEAMHA (SEQ ID NO:4). In a preferred embodiment, amino acids 578 to 711 of the furin polypeptide are substituted by the amino acid sequence AEMWHQAMEV (SEQ ID NO:5).

In yet another embodiment, an amino acid insertion builds up a loop structure, wherein the amino acids are preferably selected from the group consisting of serine (S), isoleucine (I), threonine (T), glutamic acid (E), aspartic acid (D), lysine (K), arginine(R), glycine (G), tyrosine (Y), cysteine(C), asparagine (N), proline (P), glutamine (Q) and hydroxyproline. For example, the amino acids 558 to 738, preferably amino acids 578 to 711 are substituted by the amino acid sequences SYNPG (SEQ ID NO:6), SYQPD (SEQ ID NO:7) or GSPYQTNGPS (SEQ ID NO:8). In a preferred embodiment, amino acids 578 to 711 of the furin polypeptide are substituted by the amino acid sequence GSPNSQPYDG (SEQ ID NO:9).

The selection of amino acids for forming looped and helical structures is well known to the skilled person (Lehninger A., "Biochemie", VCH, 1985, pp. 102–107).

In an alternative embodiment, the arginine at amino acid position 683 of the furin sequence can be replaced by any of the amino acids, preferably by lysine, glutamic acid or isoleucine.

Nucleic Acids and Vectors

Another embodiment of the invention provides polynucleotides which encode the furin polypeptides of the present invention. The nucleic acids used in such polynucleotides may be DNA and/or RNA.

A full-length furin polynucleotide as well as any derivatives thereof encoding a furin polypeptide having proteolytic activity can be used as the starting material for the construction of the furin polypeptides of the present invention. The cDNA sequence encoding native human furin was published by van den Ouweland, A. M. W. et al. (Nucleic Acid Res., 1990, 18(3), p. 664) and Fuller R. S. et al. (Science, 1989, 246:482). Such a furin polynucleotide can originate from any mammalian species, preferably from human, porcine or bovine sources.

The polynucleotide is expressed by a vector that provides the appropriate elements for the heterologous expression of said DNA or RNA. The expression vector comprises, for example, a transcriptional regulatory region and a translational initiation region functional in a host cell, a DNA sequence encoding for the furin polynucleotide of the present invention and translational and transcriptional termination regions functional in said host cell, wherein expression of said nucleic sequence is regulated by said initiation and termination regions.

The expression vector may also contain elements for the replication of said DNA or RNA. The expression vector may be a DNA or an RNA vector. Examples for DNA cloning and expression vectors are pBSSKII (Short, J. M., Fernandez, J. M., Sorge, J. A. and Huse, W. D. Lambda ZAP, 1988, Nucleic Acids Research 16 (15), 7583–7600; Alting. Mees, M. A., and Short, J. M., 1989, Nucleic Acids Research 17 (22), 9494), pBPV, pSVL, pCMV, pRc/RSV, myogenic vector systems (WO 93/09236) or vectors derived from viral systems, for example from vaccinia virus, adenoviruses, adeno-associated virus, herpesviruses, retroviruses or baculoviruses. Examples for RNA expression vectors are vectors derived from RNA viruses like retroviruses or flaviviruses.

In some instances it might be desirable to have a plurality of copies of the gene expressing the protein precursor in relation to the furin polypeptide, or vice versa. This can be achieved in ways well described in the prior art. Alternatively, one can employ two transcriptional regulatory regions having different rates of transcriptional initiation or different promoters, providing for enhanced expression of either the furin polypeptide according to the invention or the expression of the precursor polypeptide and/or a further polypeptide which is not to be proteolytically processed by furin.

The expression vector containing the polynucleotide which encodes the modified furin polypeptide according to the present invention can be used to transform host cells which then produce said polypeptide. The transformed host cells can be grown in a cell culture system to produce said polypeptide in vitro.

For some specific applications in gene therapy, i. e. when the nucleic acid per se is injected into an organ of a mammal, the nucleic acid, DNA as well as RNA, may be chemically modified. The chemical modifications may be modifications that protect the nucleic acid from nuclease digestion, for example by stabilizing the backbone or the termini.

The expression vector containing the nucleic acid which encodes a furin polypeptide of the present invention can further be administered to a mammal without prior in vitro transformation into host cells. The practical background for this type of gene therapy is disclosed in several patent applications, for example in WO 90/11092. The expression vector containing said nucleic acid is mixed with an appropriate carrier, for example a physiological buffer solution, and is injected into an organ, preferably skeletal muscle, the skin or the liver of a mammal.

Host Cells

The modified furin polypeptide according to the present invention is preferably produced by recombinant expression. It can be prepared by means of genetic engineering with expression systems known to the art, such as, for instance, permanent cell lines or viral expression systems. Permanent cell lines are prepared by stable integration of the extraneous DNA into the host cell genome of, e.g., vero, MRC5, CHO, BHK, 293, HEK 293, Sk-Hep1, liver cells, kidney cells, fibroblasts, keratinocytes or myoblasts, hepatocytes or stem cells, for example hematopoietic stem cells, or by an episomal vector derived, for example, from papilloma virus.

Alternatively, cell lines having no endogenous furin activity can be used (Moehring J. M. and Moehring T. J., Infect.Immun., 41, 1983, pp. 998–1009). For example, CHO-RPE40 or FD11-CHO-cells can be used. Therein, the proteolytic activity of the transfected furin of the invention can be easily measured, avoiding the background activity of endogenous furin.

Viral expression systems, such as, for instance, the vaccinia virus, baculovirus or retroviral systems, can also be employed. As cell lines, vero, MRC5, CHO, BHK, 293, Sk-Hep1, gland, liver or kidney cells are generally used. Eukaryotic expression systems, such as yeasts, endogenous glands (e.g. glands of transgenic animals) and transgenic animals can also be used for the expression of the furin polypeptides according to the present invention. For the expression of recombinant proteins, CHO-DHFR-cells have proved particularly useful (Urlaub et al., Proc.Natl.Acad.Sci., USA, vol 77, pp. 4216–4220, 1980).

The furin polypeptides according to the present invention are expressed in the respective expression systems under the control of suitable promoters. For expression in eukaryotes, known promoters are suitable, such as SV40, CMV, RSV, HSV, EBV, β-actin, hGH or inducible promoters such as hsp or metallothionein promoter.

In a preferred embodiment the present invention provides a method for the production of a furin polypeptide according to the present invention and a precursor polypeptide. Preferably, the furin polypeptide is coexpressed with von Willebrand factor protein and/or Factor VIII protein.

In a further aspect the invention provides a method for the production of a furin polypeptide according to the present invention. This method comprises growing in a nutrient medium a host cell comprising an expression vector which comprises, in the direction of transcription, a transcriptional regulatory region and a translational initiation region functional in a host cell, a DNA sequence encoding a furin polypeptide of the invention, and translational and transcriptional termination regions functional in said host cell. The expression of this DNA sequence is regulated by the initiation and termination regions. The method can further include measuring the secretion rate of expressed furin polypeptides with proteolytic activity and isolating host cells expressing furin polypeptides showing reduced secretion compared to host cells expressing wild-type furin.

Pharmaceutical Preparation

The furin polypeptide according to the present invention can be provided as a pharmaceutical preparation having a modified furin polypeptide according to the present invention as a single component preparation or in combination with other components as a multiple component system. In a particular embodiment, a furin polypeptide of the invention can be combined with pro-proteins, for example von Willebrand Factor.

Specific Activity

According to one aspect of the present invention, the furin polypeptide of the invention has a furin proteolytic activity of at least 50%, preferably at least 100% compared to the proteolytic activity of wild-type furin protein, such as wild-type human furin.

The evaluation of proteolytic activity can be performed by any suitable test, for example by using fluorogenic substrates which are comprised of a dibasic cleavage site for which furin is specific (Preininger A. et al., 1999, Schlokat U. et al., 1996, Biotechnol. Appl. Biochem., vol. 24, pp. 257–267). Alternatively the proteolytic activity can also be measured by incubating furin with pro-proteins, for example pro-rvWF, for a sufficient time. The degree of pro-rvWF processing can be analysed by Western blotting.

Secretion Rate

The secretion rate can be defined as the amount of secreted furin polypeptide (shed furin) which accumulates in a cell culture medium within a given time. The reduction in the secretion rate of the modified furin polypeptide according to the present invention is at least 25%, preferably at least 50%, more preferably at least 90%, most preferably 100% compared to the secretion rate of recombinantly expressed furin having the wild-type sequence (such as wild-type human furin) or furin lacking the transmembrane and/or cytoplasmic region.

For example, the secretion rate can be measured by immunological reactivity with anti-furin antibodies. A suitable antibody can be directed against the catalytic domain of furin (Preininger et al., 1999)

Isolation Methods

The furin polypeptide according to the present invention can be isolated from cells by lysis and further purified by conventional methods, optionally in the presence of protease inhibitors. The purification can be done by chromatographic methods known in the art, preferably by affinity chromatography, using antibodies against the furin polypeptide or by coupling the furin polypeptide to a His-Tag group and selectively binding the protein on $Ni^{2+}$-NTA agarose (Preininger et al., 1999)

Due to the fact that the proteolytic characteristics of the furin polypeptides of the present invention compared to wild type furin are substantially unaltered, proteins that are processed by wild-type furin can also be processed by the furin polypeptides of the invention, i.e. proteins with paired amino acid residues can serve as a substrate. Examples of precursor molecules for use in the present invention can include, but are not limited to, von Willebrand Factor; Factor IX, protein C, protein S, prothrombin, Factor X, Factor VII, transforming growth factor (TGF) beta and its superfamily, including activin and inhibin, bone morphogenetic proteins (BMP), insulin, relaxin, growth factors like platelet derived growth factor (PDGF), nerve growth factor (NGF), and virus polypeptides including those from cytomegalovirus (CMV), human immunodeficiency virus and herpes simplex virus.

The invention is illustrated in the subsequently described examples. Variations within the purview of one skilled in the art are to be considered to fall within the scope of the present invention. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. The following examples illustrate the present invention but do not limit the scope of the invention in any way.

EXAMPLES

1. Construction of Furin R683A

Full length furin mutant R683A, harboring the amino acid alanine instead of the native arginine at position 683, was constructed using a PCR-based approach with overlapping extended primers (Ho et al., 1989, Gene, 77, pp. 51–59). Initially, two standard PCR reactions were performed using plasmid pCMV-furin wt (harboring the furin wild-type cDNA) as template and primer pairs 4953 (5' GGGGGATC-CCTCTGGCGAGTGG 3') (SEQ ID NO:10) and 5210 (5' CGGGGACTCTGCGCTGCTCTG 3') (SEQ ID NO:11) or 5209 (5' CAGAGCAGCGCAGAGTCCCCG 3') (SEQ ID NO: 12) and 4954 (5' GGGGGATCCCCGCGGCCTAGG 3') (SEQ ID NO: 13), where 5210 and 5209 are the inner complementary extended primers introducing the mutation, and 4953 and 4954 are the outer primers containing a Bam HI restriction site. In a second PCR round, the two purified amplification products of the initial PCR reactions were combined for overlap extension in the presence of the two outer primers 4953 and 4954. The final purified PCR product was digested with Bam HI and was used to replace the wild-type Bam HI fragment in plasmid pCMV-furin wt.

2. Construction of Furin Deletion Mutants Helix 10, Loop 10 and 578–711

Furin expression constructs Helix 10 (comprising a deletion of amino acid residues 578–711 replaced by 10 helical structured residues), Loop 10 (comprising a deletion of amino acid residues 578–711 replaced by 10 loop structured residues) and 578–711 (comprising a deletion of amino acid residues 578–711) were generated by inverse PCR. For that purpose, the internal 1176 bp Bam HI fragment of wild-type furin was subcloned into the Bam HI site of vector pBS SKII(+) (Stratagene). The resulting plasmid pBS/fur1176 was used as the template for the inverse PCR reactions of the individual constructs. In the case of Helix 10 and Loop 10, the specific sense and reverse primers each contained at their 5'-end an additional overhanging 15 nucleotides coding for 5 helical or loop structured amino acids. The following primer sets were used: for Helix 10, sense primer 5699 (5' CAGGCCATGGAGGTGCACCTGCCTGAG-GTGGTGGCCGGCCTCAGC 3') (SEQ ID NO.14) and reverse primer 5700 (5' GTGCCACATCTCGGCCCCCT-CAGGGGCGGTGCCATAGAGTACGAG 3' (SEQ ID NO:15), for Loop 10, sense primer 5701 (5' CAGCCCTAC-GACGGCCACCTGCCTGAGGTGGTGGCCG-GCCTCAGC 3') (SEQ ID NO:16) and reverse primer 5702 (5' GCTGTTGGGGCTGCCCCCCTCAGGGGCG-GTGCCATAGAGTACGAG 3') (SEQ ID NO:17), and for 578–711, sense primer 5723 (5' CACCTGCCTGAGGTG-GTGGCC 3') (SEQ ID NO:18) and reverse primer 5724 (5' CCCCTCAGGGGCGGTGCCATA 3') (SEQ ID NO:19). The resulting PCR-fragments were purified, treated with T4 polynucleotide kinase (New England Biolabs), religated with T4 DNA-ligase (Roche) and transformed into E. coli strain XL1 Blue MRF' (Stratagene). Positive clones, harboring the introduced mutation were selected by sequencing, and the mutated BamHI fragment was used to replace the wt 1176bp BamHI fragment in pCMV-furin wt.

Generally, amplification of the target sequences was routinely carried out within 30 PCR cycles using 10–20 ng template DNA in a total volume of 100 μl containing 30 pMol of each primer, 200 μM of each dNTP, 2 mM MgSO$_4$ in the supplied 10×PCR buffer and 2.5 U Vent$_R$® DNA polymerase (New England Biolabs) at 55° C. annealing and 72° C. extension temperatures. PCR-fragments were purified using QIAEX II Gel Extraction Kit (Qiagen) according to the supplier's instructions.

The Helix 10 insertion into the furin deletion mutant Δ578–711 comprises the amino acid sequence AEM-WHQAMEV (SEQ ID NO:20). The Loop 10 insertion into the furin deletion mutant Δ578–711 comprises the amino acid sequence GSPNSQPYDG (SEQ ID NO:21).

3. Transfection, Cell Culture and Protein Harvest

Furin constructs were transiently expressed in 293 HEK (human embryonic kidney fibroblasts; ATCC CRL 1573) and FD11-CHO-rvWF cells (FD11-CHO are furin deficient cells). The cells were grown in DMEM/Ham's F12 (1:1) medium (Life Technologies) supplemented with 10% fetal calf serum (full medium) . For transfection, cells were grown to 50–75% confluency on 5 cm culture dishes (Costar) and transfected by calcium phosphate coprecipitation as described previously (Fischer et al., 1994). Transient transfections were carried out with 20 $\mu$g of expression plasmid.

Recombinant protein was harvested by applying serum-free full medium to the transfected cells upon confluency (generally 48 hours post-transfection), after washing them twice with PBS ($Ca^{2+}$ and $Mg^{2+}$ free, Life Technologies). Conditioned medium was collected and cleared by centrifugation. Adherent cells were trypsinized, washed with PBS and the total cell number was determined by a CASY counter (Schärfe Systems, Germany) employing a 30 $\mu$m capillary. Cell extracts were prepared by lysing the cells at a concentration of $5\times10^7$ cells/ml lysis buffer, containing 20 mM Tris-HCl, pH7.5, 150 mM NaCl, 1 mM EDTA and 0.5% Tritone® X-100. After incubation for 30 min at 4° C., lysates were cleared by centrifugation for 15 min at 10,000×g at 4° C.

4. Western Blotting

Samples were reduced and denatured, resolved by SDS-PAGE on 4% stacking/8% or 10% separation gels, and visualized by Western blotting as described (Schlokat et al., 1996). Conditioned medium derived from FD11-CHO-rvWF transient transfections was concentrated 20× by speed-vac centrifugation prior to loading. Lysates were applied per slot on SDS-PAGE equivalent to 7.5×10 cells. For the detection of furin molecules, murine monoclonal antibody MON-148 (Alexis) directed against the catalytic domain of furin and alkaline phosphatase conjugated to anti-mouse IgG goat sera (Sigma) as the second antibody was used. Recombinant vWF was visualized employing rabbit anti-vWF antiserum (DAKO) and alkaline phosphatase conjugated to anti-rabbit IgG goat sera (Promega) as the second antibody.

FIG. 3 shows the amount of shed furin in conditioned medium of transiently transfected FD11-CHO-rvWF cells. The conditioned medium was concentrated 20× and applied and denatured on 4% stacking/10% separation SDS-PAGE gel. The Western blot was visualized with MON-148 and AP-conjugated anti-mouse IgG antibody.

As a control, a pCMV vector, wild-type furin polypeptide and Δ577G-4×G-10×H were used. The furin construct Δ577G-4×G-10×H was prepared according to Preininger et al. (1999).

The figure clearly shows that the furin constructs according to the invention do not show any shedding, i.e. the secretion rate of the molecules into the medium is substantially reduced compared to rfurin having the wild-type sequence or furin lacking the transmembrane and cytoplasmic domains.

5. Analysis of in vitro Furin Activity in Conditioned Medium

Functional activity of shed furin molecules was determined by fluorogenic substrate as described previously (Schlokat et al., 1996).

6. Evidence of Intracellular rfurin Activity

FD11-CHO-rvWF cells stably expressing furin mutant R683A or wild-type furin were established by cotransfection using 20 $\mu$g furin expression plasmid and 1 $\mu$g selection plasmid pCMV-hyg mediating resistance to hygromycin B (Roche). Resistant clones were isolated two weeks after transfection and stabilized by subcloning under selective pressure. Three FD11-CHO-rvWF/R683A clones (clone 1, 2 and 3) differing in the amount of secreted rfurin and consequently showing variable degrees of rvWF precursor processing were selected.

Intracellular furin activity was demonstrated by correlating the degree of rvWF precursor processing and the presence of shed rfurin in FD11-CHO-rvWF/R683A conditioned media over a time period of 24 hours. As controls, FD11-CHO-rvWF/furin wt and FD11-CHO-rvWF cells were used. Cells were grown in 6-well dishes (one well/timepoint) until confluency, and washed two times with PBS before serum-free medium was applied for a time period of 4, 8, 16 and 24 hours. Conditioned medium was cleared by centrifugation and concentrated 20× for the detection of shed rfurin. Estimation of rvWF precursor processing was done by Western blot.

FIG. 4 shows the processing of rvWF precursor in transiently transfected FD11-CHO-rvWF cells. 100 ng rvWF was applied per lane. Probes were reduced denatured and applied on 4% stacking/5% separating SDS-PAGE gel. The Western blot was developed with polyclonal rabbit-anti-vWF and AP-conjugated anti-rabbit IgG antibody. Although the cells were only transiently transfected, the R683A, Helix 10, Loop 10 and Δ578–711 furin constructs evidence proteolytic activity. The term transiently transfected reflects a genetically non-homogenous, mixed cell population. Depending on the transfection efficiency, only some of the cells are transfected.

FIG. 5 (comprising FIGS. 5A–5C) shows furin expression in transiently transfected HEK293 cells:

FIG. 5A shows shed furin in conditioned medium of transiently transfected HEK293 cells. 15 $\mu$l of conditioned medium were applied per slot. Probes were reduced and denatured and denatured and applied on 4% stacking/10% separating SDS-PAGE. The Western blot was developed with MON-148 and AP-conjugated anti-mouse IgG antibody.

Figure 5:
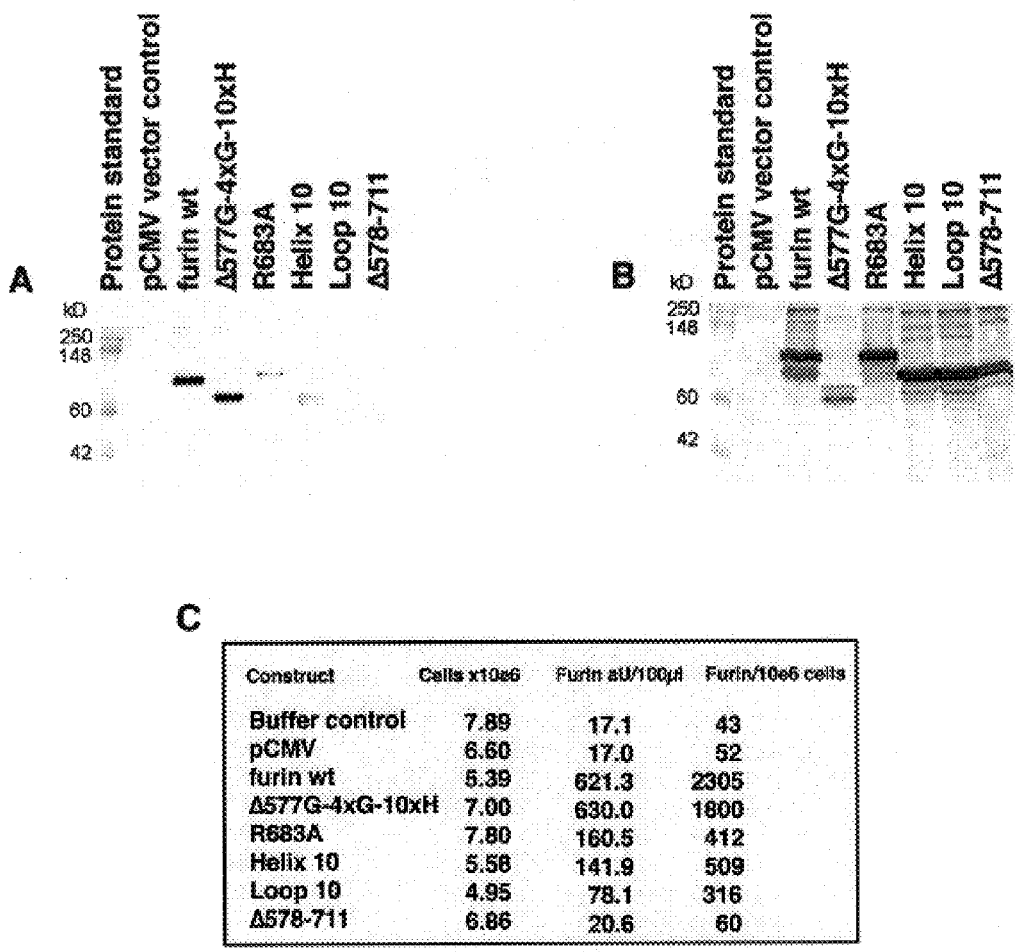
FIGS. 5A–5C show furin expression in transiently transfected HEK 293 cells.

FIG. 5B shows the measurement of intracellular rfurin in HEK293 lysates. 7.5×10e5 cell equivalents were applied per slot.

FIG. 5C shows the results of an in vitro assay using conditioned medium and a fluorogenic substrate.

FIG. 5A shows that the amount of secreted furin polypeptides in the medium detectable by a specific antibody is highly reduced. This is confirmed by the in vitro activity measurements shown in FIG. 5C. The data of FIG. 5B show that the furin polypeptides are located intracellularly.

Figure 6:
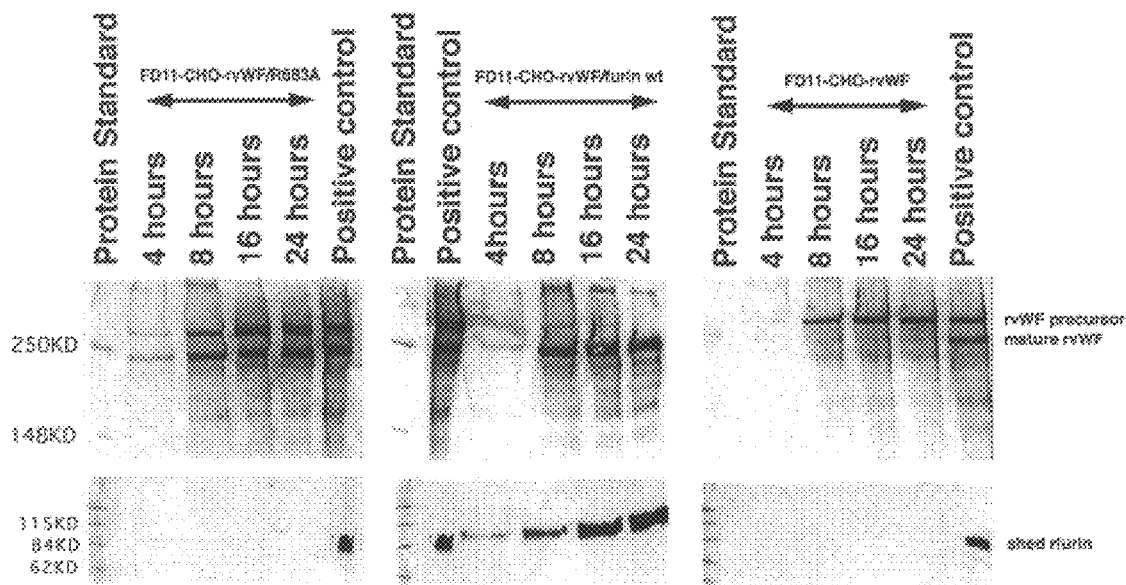
FIG. 6 is a photograph of three SDS-PAGE gels showing the correlation between the degree of rvWF precursor processing and the presence of shed furin in conditioned medium.

FIG. 6 shows the intracellular proteolytic activity of the furin construct R683A. The degree of rvWF precursor protein processing and the presence of shed rfurin in the conditioned medium is compared. The figure shows that significant proteolytic processing of vWF protein occurs even though no shed furin is detected in the medium. This indicates that this furin polypeptide is proteolytically active even though it is not secreted into the medium.

The upper lane is a vWF western blot, wherein 100 ng rvWF is applied per lane. As a positive control, CHO-rvWf was used.

The lower lane is a furin western blot of conditioned medium. The material was concentrated 20× per lane. As a positive control, shed wild-type rvWF was used.

We claim:

1. A furin polypeptide comprising amino acids, said amino acids having a sequence which comprises a modification compared to the amino acid sequence of wild-type furin as set forth in SEQ ID NO:1, wherein said modification is present between amino acids Ala 557 and Leu713 inclusive, of wild-type furin, and further wherein said modification results in the formation of a loop or alpha-helix structure between amino acids Ala 557 and Leu713 of wild-type furin.

2. A furin polypeptide according to claim 1 wherein said modification is between amino acids 577 and 713.

3. A furin polypeptide according to claim 1 wherein said modification is a substitution of from 5 to 30 amino acids.

4. A furin polypeptide according to claim 1 wherein said modification is a substitution of 10 or more amino acids that results in the formation of a helix or loop structure within the mutant furin polypeptide.

5. A furin polypeptide according to claim 1 wherein said modification comprises adding or substituting amino acids at a furin amino acid position, wherein the added or substituted amino acids at the position are selected from the group consisting of alanine (A), leucine (L), phenylalanine (F), tryptophan (W), methionine (M), histidine (H), glutamine (Q) and valine (V).

6. A furin polypeptide according to claim 1 wherein said modification comprises adding or substituting amino acids at a furin amino acid position, wherein the added or substituted amino acids at the position are selected from the group consisting of serine (S), isoleucine (I), threonine (T), glutamic acid (E), aspartic acid (D), lysine (K), arginine(R), glycine (G), tyrosine (Y), cysteine(C), asparagine (N), glutamine (Q), proline (P) and hydroxyproline.

7. A furin polypeptide according to claim 1 wherein amino acids 578 to 711 are deleted.

8. A furin polypeptide according to claim 1 wherein the amino acids between amino acids 577 and 713 are replaced by amino acids comprising the sequence AEMWHQAMEV.

9. A furin polypeptide according to claim 1 wherein the amino acids between amino acids 577 and 713 are replaced by amino acids comprising the sequence GSPNSQPYDG.

10. A furin polypeptide according to claim 1 wherein said modification is at Arg683.

11. A recombinant DNA molecule encoding a furin polypeptide according to claim 1.

12. A recombinant expression vector comprising a DNA molecule according to claim 11 operably linked to a heterologous expression control sequence permitting expression of said furin polypeptide.

13. A host cell comprising a recombinant DNA expression vector according to claim 12.

14. A transformed host cell according to claim 13 which additionally comprises a polynucleotide encoding at least one recombinantly expressed precursor polypeptide, wherein said polypeptide is a substrate for the encoded furin polypeptide.

15. A method for the production of a furin polypeptide according to claim 1, said method comprising:

(a) growing in a nutrient medium a host cell comprising an expression vector, said expression vector comprising, in order in the direction of transcription:
   a transcriptional regulatory region and a translational initiation region which is functional in said host cell,
   a DNA sequence encoding a mutant furin polypeptide according to claim 1, and
   translational and transcriptional termination regions functional in said host cell,
   wherein expression of said DNA sequence is regulated by said initiation and termination regions;
(b) measuring the secretion rate of furin polypeptides with proteolytic activity; and
(c) isolating host cells expressing furin polypeptides showing reduced secretion compared to host cells expressing wild type furin.

\